(12) United States Patent
Kasen et al.

(10) Patent No.: US 6,675,635 B2
(45) Date of Patent: Jan. 13, 2004

(54) SYSTEM AND METHOD FOR DETERMINING OIL QUALITY

(75) Inventors: Jon E. Kasen, E. Peoria, IL (US); Michelle A. Lee, Edelstein, IL (US); Philip H. McCluskey, Dunlap, IL (US)

(73) Assignee: Caterpillar Inc, Peoria, IL (US)

( * ) Notice: Subject to any disclaimer, the term of this patent is extended or adjusted under 35 U.S.C. 154(b) by 0 days.

(21) Appl. No.: 10/124,555

(22) Filed: Apr. 17, 2002

(65) Prior Publication Data

US 2003/0196479 A1 Oct. 23, 2003

(51) Int. Cl.⁷ ................................................ G01N 11/00
(52) U.S. Cl. ...................................... 73/53.05; 73/54.01
(58) Field of Search ............................ 73/53.05, 54.02, 73/54.01, 54.42, 54.43

(56) References Cited

U.S. PATENT DOCUMENTS

| | | | |
|---|---|---|---|
| 4,675,662 A | 6/1987 | Kondo et al. | |
| 4,785,287 A | 11/1988 | Honma et al. | |
| 4,858,127 A * | 8/1989 | Kron et al. | 364/413.07 |
| 4,890,482 A * | 1/1990 | Maini | 73/55 |
| 5,750,887 A | 5/1998 | Schricker | |
| 5,789,665 A | 8/1998 | Voelker et al. | |
| 5,986,546 A | 11/1999 | Kramer | |
| 5,987,976 A | 11/1999 | Saranganpani | |
| 6,050,130 A | 4/2000 | Kramer | |
| 6,216,528 B1 * | 4/2001 | Carrell et al. | 73/54.01 |
| 6,223,589 B1 | 5/2001 | Dickert et al. | |
| 6,286,363 B1 * | 9/2001 | Discenzo | 73/53.01 |
| 6,508,107 B2 * | 1/2003 | Carrell et al. | 73/54.02 |
| 6,553,812 B2 * | 4/2003 | Park et al. | 73/54.01 |
| 6,561,010 B2 * | 5/2003 | Wilson et al. | 73/54.04 |
| 2001/0013247 A1 * | 8/2001 | Wilson et al. | |
| 2002/0011095 A1 * | 1/2002 | Park et al. | |

* cited by examiner

Primary Examiner—Hezron Williams
Assistant Examiner—C D Garber
(74) Attorney, Agent, or Firm—Mike Huber

(57) ABSTRACT

The oil quality used in a machine, vehicle or system can be determined in response to determining a temperature and pressure within an oil supply. Once the oil quality is determined, an oil quality warning light can be activated, indicating the need to change the oil.

18 Claims, 1 Drawing Sheet

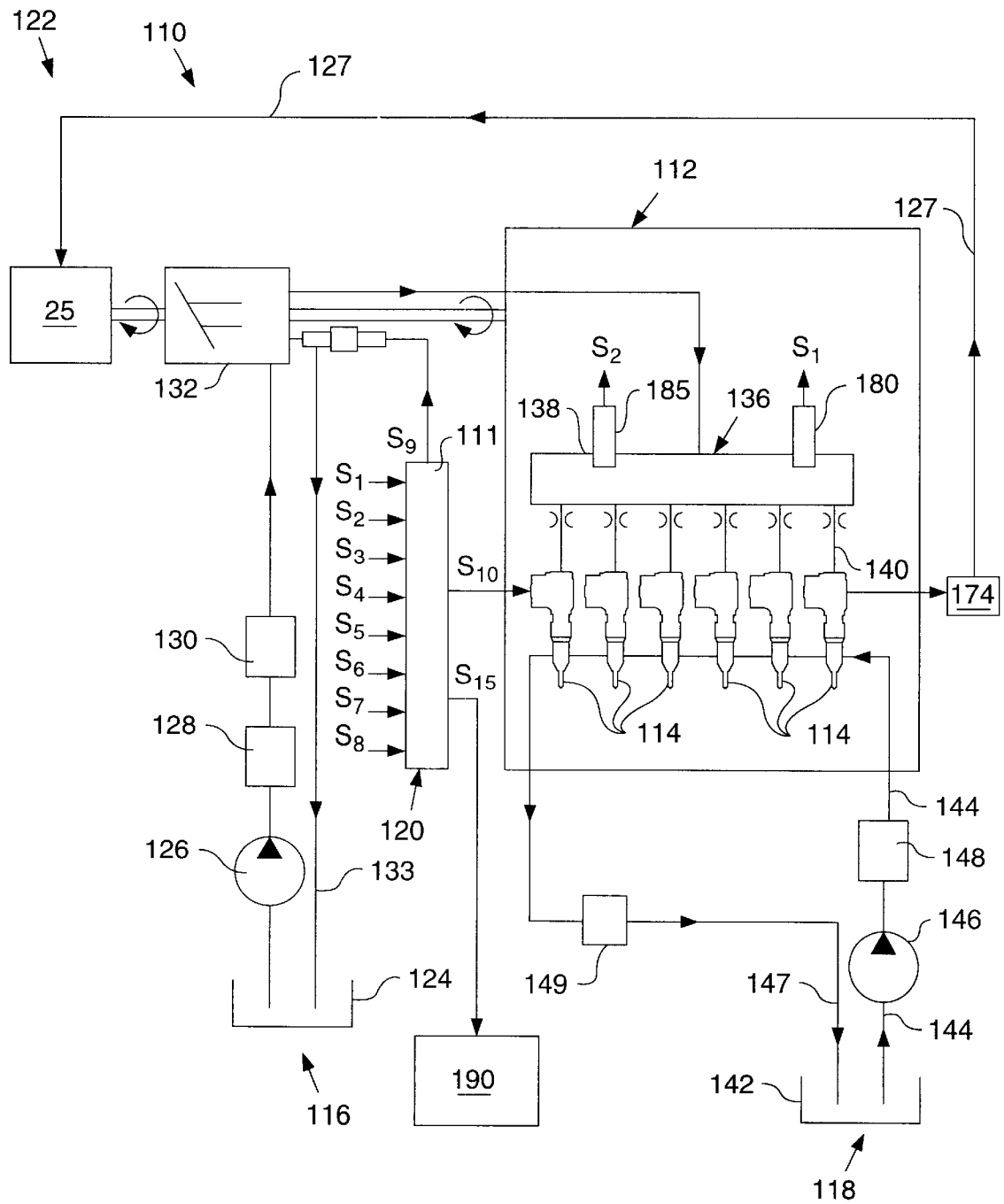

SYSTEM AND METHOD FOR DETERMINING OIL QUALITY

TECHNICAL FIELD

The present invention relates to determining the quality of oil used in a machine or apparatus.

BACKGROUND

Oil is used in numerous applications and is commonly used as a lubricant in engines. Due to the broad range of engines and operating environments, lubrication oil is available in a variety of different viscosities (formulations, weights, or grades). For example, lubrication oil could be a single viscosity oil, such as SAE 30 base oil, which has a viscosity of 30 at a set testing temperature or lubrication oil could be a multi-viscosity oil, such as 15W40, 0W30, or 10W30. With multi-viscosity oils, the first number indicates a first viscosity at a first temperature (a cold temp.) and the second number indicates the oil's second viscosity at a second temperature (a hot temp.) Multi-viscosity oils are beneficial in engine use to help handle the diverse operating environments, such as cold start.

In some devices or engine systems, lubrication oil is also used as an actuation fluid for hydraulically actuated devices. For example, because lubrication oil is a common fluid source in engine systems, it is relatively easy to employ for hydraulic "muscle" in hydraulically actuated electronically controlled unit injectors or hydraulically actuated or partially actuated valves. By using hydraulic power, actuation events can be controlled independently of the engine speed (eliminating dependency on the cam shaft) and enhance engine performance. Specifically, in unit injectors, oil is pressurized to relatively high levels and is used in conjunction with an intensifier piston to pressurize fuel to injection pressure. With valves, the pressurized oil can be used to open intake or exhaust valves.

Although lubrication oil is an excellent engine lubricant or actuation fluid, it does have one major drawback, it has a limited life and must be replaced regularly. After prolonged use, the oil can experience viscosity breakdown or can become very dirty and potentially more viscous due to small pieces of metal or dirt getting in the oil. When oil breaks down or becomes dirty, several negatives exist. First, the oil does not provide the desired lubrication and can result in increased engine wear and potentially permanent engine damage. Second, if the oil is being used as an actuation fluid, the oil does not have the anticipated viscosity which results in the oil not responding as expected. Subsequently, this alters the timing, quantity and rate of actuation events, which decreases engine efficiency and may increase emissions.

Therefore, it is beneficial to know when the oil's quality is unacceptable. Generally, engines or systems do not have any type of oil quality warning device. Instead, it is just recommended that the oil be changed every so often, even thought the actual oil quality is not known. This can result in lost use of good oil or the over use of bad oil.

There have been many different methods developed to try and determine the quality of oil in an engine or system; however, they do not capitalize on existing hardware of system operation and often require additional hardware and housings or cavities in an already complicated engine system. For example in U.S. Pat. No. 6,050,130, issued to Kramer, an additional housing is installed in a pneumatic brake system having a supply of air contaminated with oil. The surface of the housing accumulates a film of oil and an additional sensor directs an electromagnetic waves against the surface of the housing. The sensor then receives a reflected wave back from the surface and produces an oil contamination signal based upon the altered characteristics of the reflected wave.

The present invention is intended to address one or more of the above problems.

SUMMARY OF THE INVENTION

In the first embodiment of the present invention, a method for determining oil quality comprises measuring a temperature and oil supply, measuring a pressure in the oil supply and determining the oil quality in response to the measuring steps.

In the second embodiment of the present invention, a system for determining an oil quality comprises a temperature sensor, a pressure sensor and an electronic control module connected to the sensors, wherein the electronic control unit receives a signal from the sensors and determines the oil quality in response to those signals.

In the third embodiment of the present invention, a method for determining oil quality comprises determining an oil grade of the oil supply, measuring the temperature of the oil supply, measuring first pressure of the oil supply, measuring a duration of an event drawing oil from the oil supply, measuring a second pressure of the oil supply, estimating a pressure drop of the oil supply, determining an actual pressure drop of the oil supply in response to measuring the first and second pressures, comparing the actual pressure drop to the estimated pressure drop, and determining an oil quality in response to a comparing step.

In the forth embodiment of the present invention, a method for determining oil quality comprises determining a pressure drop in an oil supply, determining temperature in an oil supply and determining oil quality in response to the determining steps.

BRIEF DESCRIPTION OF THE DRAWINGS

FIG. 1 is a schematic illustration of a fuel system according to one embodiment of the present invention.

DETAILED DESCRIPTION

FIG. 1 illustrates an embodiment of a hydraulically actuated electronically controlled fuel injection system 110 in an example configuration as adapted for a direct-injection diesel-cycle internal combustion engine 112. Fuel system 110 includes one or more hydraulically-actuated electronically-controlled fuel injectors 114, positioned in a respective cylinder head bore (not shown) of engine 112. Fuel system 110 includes a first source of pressurized fluid flow 116 for supply of actuating fluid to each injector 114, a second source of pressurized fluid flow 118 for supplying fuel to each injector, a computer 120 for electronically controlling the fuel injection system and an apparatus 122 for re-circulating actuation fluid leaving each of the injectors.

The first fluid source 116 preferably includes an actuating fluid sump 124, a relatively low pressure actuating fluid transfer pump 126, an actuating fluid cooler 128, one or more actuation fluid filters 130, a high pressure pump 132 for generating relatively high pressure in the actuation fluid and at least one relatively high pressure actuation fluid manifold 136. A oil rail passage 138 is arranged in fluid communication with the outlet from the relatively high pressure actuation fluid pump 132. A rail branch passage 140 connects the actuation fluid inlet of each injector 114 to the high pressure oil rail passage 138.

Actuation fluid leaving an actuation fluid drain of each injector 114 enters a re-circulation line 127 that carries the same to the actuation fluid re-circulating apparatus 122. A portion of the re-circulated actuation fluid is channeled to high pressure actuation fluid pump 132 and another portion is returned to actuation fluid sump 124 via re-circulation line 133.

In a preferred embodiment, the actuation fluid is engine lubricating oil and the actuation fluid sump 124 is an engine lubrication oil sump. This allows the fuel injection system to be connected as a parasitic subsystem to the engine's lubricating oil circulation system.

The second fluid source 118 preferably includes a fuel tank 142, a fuel supply passage 144 arranged in fluid communication between fuel tank 142 and the fuel inlet of each injector 114, a relatively low pressure fuel transfer pump 146, one or more fuel filters 148, a fuel supply regulating valve 149, and a fuel circulation and return passage 147 arranged in fluid communication between injectors 114 and fuel tank 142.

The computer 120 preferably includes an electronic control module (ECM) 111 including a microprocessor and memory. As is known to those skilled in the art, the memory is connected to the microprocessor and stores instruction sets, variables and maps (or look-up tables) which provide information or instructions based upon certain known conditions. Associated with the microprocessor and part of the ECM 111 are various other known circuits such as power supply circuitry, signal conditioning circuitry and solenoid driver circuitry, among others. The ECM 111 controls a variety of engine functions and injection parameters including: 1) the fuel injection timing; 2) the total fuel injection quantity during an injection cycle; 3) the fuel injection pressure; 4) the number of separate injections or injection segments during each injection cycle; 5) the time intervals between the injection segments; 6) the fuel quantity of each injection segment during an injection cycle; 7) the actuation fluid pressure; 8) current level of the injector waveform; and 9) any combination of the above parameters. ECM 111 receives a plurality of sensor input signals S1–S8, which correspond to known sensor inputs, such as engine operating conditions including engine speed, engine temperature, pressure of the actuation fluid, temperature of the actuation fluid, load on the engine, etc., as well as desired operating conditions such as desired engine speed, that are used to determine the precise combination of injection parameters for a subsequent injection cycle.

For example, a rail temperature sensor 180 is connected to oil rail passage 138 and produces a signal, designated S1, responsive to the temperature of the actuating fluid. The signal S1 is input into the ECM 111. Another example of an engine sensor input is a rail pressure sensor 185 shown connected to the high pressure oil rail passage 138 for producing a high pressure signal S2 responsive to the pressure of the actuating fluid. Commonly, the signals S1 and S2 are voltages created by the sensor where the voltage created depends upon the measured condition.

In this example, ECM 111 issues control signal S9 to control the actuation fluid pressure and a fuel injection signal S10 to energize a solenoid within a fuel injector thereby controlling fluid control valve(s) within each injector 114 and causing fuel to be injected into a corresponding engine cylinder. Each of the injection parameters are variably controllable, independent of engine speed and load. In the case of injector 114, control signal S10 is a fuel injection signal that is a computer commanded current to the injector solenoid. In controlling injector 114, ECM 111 can control injector 114 in a variety of ways using signal S10 including using multiple signals, such as sending a signal to turn on, a second signal to maintain, and a third signal to turn off, or ECM 111 could simply use one signal wherein when the signal is sent to injector 114, it is on, and when the signal is terminated, injector 114 turns off.

Fuel injectors 114 are capable of multiple injections or injection segments per engine cycle. As stated previously, the ECM 111 controls when, duration and number of injections or segments for each injector 114 per engine cycle. Multiple injections or injection segments are well known in the art and may include pilots, mains, posts, and anchors.

In order to maintain proper engine performance, and more specifically, proper fuel system or lubrication system performance, oil quality must be maintained at a certain level. If the oil is not of a certain quality, it needs to be replaced. Generally, oil experiences viscosity breakdown over time. Additionally, the oil can become dirty with dirt, particles and combustion products, as a result of traveling through the engine system, which can also affect the viscosity of the oil. Poor quality oil can result in poor lubrication, causing increased engine wear or even engine break down. Further, poor quality oil can have a substantial impact on the function of the fuel system when oil is being used as the actuation fluid, as demonstrated in FIG. 1. Specifically, the quality (or viscosity) of the oil can affect the timing, rate and quantity of the injection event which can limit engine efficiency and increase emissions. Therefore, it is desirable to know when to change a system's oil.

In the system illustrated in FIG. 1, ECM 111 sends an actuation signal S10 to injector 114 when an injection is desired. This causes injector 114 to draw oil from the oil rail passage 138 to pressurize fuel for injection into the combustion chamber (not shown). Concurrently with sending the actuation signal S10, rail temperature sensor 180 measures the temperature of the oil in oil rail passage 138 and sends a signal S1 to the ECM 111. Additionally, rail pressure sensor 185 determines the oil pressure in the rail at the beginning of the injection event and sends a signal S2 to ECM 111. When the injection event is finished, ECM 111 terminates injection signal S10 and determines how long the injection event lasted. At this point, a second pressure reading is made by rail pressure sensor 185 and a signal S2 is sent ECM 111. It is preferred that the oil temperature and pressure are determined in close proximity to the oil drawing event in order to obtain the most accurate data possible; however it may be necessary to adjust the timing of the measurements in order to account for other events that may be occurring in the system.

From the data captured through the injection event, ECM 111 can determine the oil quality of system 110. In order to determine the oil quality, ECM 111 must first know or determine what type of oil (oil grade) is being used in the system. This can be done in numerous ways know to those skilled in the art. For example, the type of oil could be programmed into the system when an oil change occurs. By knowing the oil grade and the duration of the injection event (the time ECM 111 started sending signal S10 to injector 114 until the time signal S10 was terminated), ECM 111 can estimate how much oil should have been drawn into injector 114 at the specific temperature measured by rail temperature sensor 180. From this an estimated rail pressure drop can be determined. (The rail pressure drop is a result of oil being "pulled out" of the oil rail passage 138 into injector 114 to actuate an intensifier piston (not shown) to pressurize the fuel).

ECM 111 can also determine what the actual rail pressure drop was. A first rail pressure was measured by rail pressure sensor 180 at the beginning of the injection event and a second rail pressure was measured at the end of the injection event. From these two measurements, ECM 111 can determine the actual pressure drop for oil rail passage 138. ECM 111 then compares the actual pressure drop to the estimated pressure drop. If the actual rail pressure drop is outside of an acceptable, predetermined range compared to the estimated pressure drop, the oil quality is unacceptable and an oil change is necessary. If an oil change is necessary, ECM 111 can send a signal S15 to an oil quality warning light 190, which is visible by the operator of the engine or machine.

It may be desirable to average several rail pressure measurements or make several comparisons before a warning light is turned on. This will insure that the oil quality is actually undesirable and a change is necessary.

INDUSTRIAL APPLICABILITY

Oil plays a vital role in the operation of machines, vehicles and systems; providing lubrication for the system in extreme operating conditions and providing actuation "muscle" in exacting, complex fluid systems (ex. fuel systems). Oil quality determines how well a system's oil performs its necessary functions. Old, or dirty oil, can limit system performance and result in excessive wear and tear on the system. Therefore, it is important to maintain good oil quality by changing the oil when needed. By determining oil quality, and signaling the operator, the operator can know when the oil quality does not meet acceptable limits and change the oil. Maintaining good oil quality helps insure preferred system operation and extended system life.

Oil quality detection can be implemented in a variety of systems. As illustrated above, it can be used in a system using hydraulically actuated electronically controlled unit injectors, but oil quality detection can also be used for other hydraulically actuated engine systems, such as controlling engine intake and exhaust valves. Oil quality detection could also be used in automobiles for determining oil quality in a car's lubrication system.

The above illustration also showed the system using sensors that directly measured rail pressure and temperature; however, other indirect sensing methods could be used. For example, oil temperature could be measured in the sump, pump, or injector. Further, the temperature could be indirectly determined, estimated or inferred by measuring the temperature or properties of other engine components or systems, such as the coolant or engine block. Similar indirect methods could be used to measure, determine or estimate the oil rail pressure, such as monitoring pump activity or injector activity to determine the pressure drop of the oil rail.

Other aspects, features, and advantages of the present invention may be obtained from a study of this disclosure and the drawings, along with the appended claims.

What is claimed is:

1. A method for determining an oil quality comprising:
measuring a temperature in an oil supply;
measuring a pressure in said oil supply;
measuring a duration of an event drawing oil from said oil supply;
determining an oil grade for said oil supply;
determining an estimated pressure drop for said oil supply as a function of said event duration and said oil grade; and
determining said oil quality in response to said measuring temperature step, said measuring pressure step, and said estimated pressure drop.

2. The method of claim 1 further including:
determining a pressure drop in said oil supply.

3. The method of claim 1 further including:
measuring a second pressure in said oil supply;
comparing said pressure to said second pressure; and
determining a pressure drop in said oil supply.

4. The method of claim 3 further including:
measuring the time between measuring said pressure and measuring said second pressure.

5. The method of claim 1 wherein determining said oil grade includes:
inputting said oil grade.

6. The method of claim 1 further including:
determining a pressure drop in said oil supply;
comparing said pressure drop to said estimated pressure drop; and
determining said oil quality in response to said comparing step.

7. The method of claim 6 further including:
measuring a second pressure in said oil supply;
comparing said pressure to said second pressure; and
determining a pressure drop in said oil supply in response to said comparing step.

8. The method of claim 6 further including:
activating an oil quality warning light in response to said determining oil quality step.

9. A method of determining an oil quality of a oil supply comprising:
determining an oil grade of said oil supply;
measuring a temperature of said oil supply;
measuring a first pressure of said oil supply;
measuring a duration of an event drawing oil from said oil supply;
measuring a second pressure of said oil supply;
estimating a pressure drop of said oil supply;
determining an actual pressure drop of said oil supply in response to measuring said first pressure and measuring said second pressure;
comparing said actual pressure drop to said estimated pressure drop; and
determining said oil quality in response to said comparing step.

10. The method of claim 9 including:
measuring said first pressure before said event.

11. The method of claim 10 further including:
activating an oil quality warning light in response to determining said oil quality.

12. The method of claim 10 further including:
averaging said actual pressure drop over time;
comparing said averaged pressure drop to said estimated pressure drop; and
determining said oil quality in response to said comparing said averaged pressure drop to said estimated pressure drop.

13. The method of claim 9 including:
measuring said first pressure proximate in time to a start of said event.

14. The method of claim 9 including:
measuring said second pressure at an end of said event.

15. The method of claim 9 including:
measuring said second pressure proximate in time to an end of said event.

16. A method for determining an oil quality comprising the steps of:
determining a temperature of an oil supply and generating a responsive temperature signal;
determining a pressure of said oil supply and generating a responsive pressure signal;
delivering said temperature and pressure signals to an electronic control module;
determining an oil grade for said oil supply;
determining a duration of an event drawing oil from said oil supply;
determining an estimated pressure drop as a function of said event duration and said oil grade; and
determining said oil quality as a function of said temperature, said pressure, and said estimated pressure drop.

17. A method, as set forth in claim 16, wherein determining a pressure of said oil supply includes the steps of:
determining a first pressure at a first predetermined time;
determining a second pressure at a second predetermined time;
comparing said first and second pressures; and
determining a pressure drop from said first predetermined time to said second predetermined time.

18. A method, as set forth in claim 17, further including the steps of:
comparing said determined pressure drop with said estimated pressure drop; and
responsively determining said oil quality.

\* \* \* \* \*